(12) United States Patent
de Oliveira et al.

(10) Patent No.: US 10,857,088 B2
(45) Date of Patent: Dec. 8, 2020

(54) HAIR CARE SYSTEM CONCENTRATE

(71) Applicant: Dow Brasil Sudeste Industrial Ltda., Sao Paulo/Sp (BR)

(72) Inventors: Maria Rita de Oliveira, Sao Paulo (BR); Daisy de Fátima Scarparo de Sanctis, Sao Paulo (BR); Mayra Penna, Sao Paulo (BR)

(73) Assignee: Dow Brasil Sudeste Industrial Ltda., San Paulo/Sp. (BR)

( * ) Notice: Subject to any disclaimer, the term of this patent is extended or adjusted under 35 U.S.C. 154(b) by 47 days.

(21) Appl. No.: 16/308,492

(22) PCT Filed: Jun. 29, 2017

(86) PCT No.: PCT/BR2017/050169
§ 371 (c)(1),
(2) Date: Dec. 10, 2018

(87) PCT Pub. No.: WO2018/000069
PCT Pub. Date: Jan. 4, 2018

(65) Prior Publication Data
US 2019/0254953 A1  Aug. 22, 2019

Related U.S. Application Data

(60) Provisional application No. 62/355,987, filed on Jun. 29, 2016.

(51) Int. Cl.
*A61K 8/86* (2006.01)
*A61K 8/39* (2006.01)
*A61K 8/73* (2006.01)
*A61Q 5/00* (2006.01)
*A61Q 5/12* (2006.01)

(52) U.S. Cl.
CPC .............. *A61K 8/86* (2013.01); *A61K 8/39* (2013.01); *A61K 8/731* (2013.01); *A61Q 5/002* (2013.01); *A61Q 5/12* (2013.01); *A61K 2800/5422* (2013.01); *A61K 2800/5426* (2013.01)

(58) Field of Classification Search
CPC ...................................................... A61K 8/86
See application file for complete search history.

(56) References Cited

U.S. PATENT DOCUMENTS

| | | | |
|---|---|---|---|
| 6,589,517 | B1 | 7/2003 | McKelvey et al. |
| 2003/0069148 | A1 | 4/2003 | Booker et al. |
| 2004/0115155 | A1 | 6/2004 | Salvador et al. |
| 2011/0223124 | A1 | 9/2011 | Drovetskaya et al. |

FOREIGN PATENT DOCUMENTS

| | | |
|---|---|---|
| EP | 2018841 A1 | 1/2009 |
| EP | 2110117 A1 | 10/2009 |
| JP | 2016003203 A | 1/2016 |
| WO | 0191708 A1 | 12/2001 |
| WO | 03047540 A1 | 6/2003 |
| WO | 2006010440 A1 | 2/2006 |

*Primary Examiner* — Benjamin J Packard
(74) *Attorney, Agent, or Firm* — Thomas S. Deibert

(57) ABSTRACT

A hair care system concentrate is provided, comprising: 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and, 10 to 35 wt % a polyethylene glycol diester of stearic acid. Also provided is a method of making a hair care system concentrate.

9 Claims, No Drawings

HAIR CARE SYSTEM CONCENTRATE

The present invention relates to a hair care system concentrate. In particular, the present invention relates to a hair care system concentrate containing 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and, 10 to 35 wt % a polyethylene glycol diester of stearic acid. The present invention also provides a method of making a hair care system concentrate.

When the cuticle of a hair is damaged, the hair becomes dry, loses shine and luster. Other signs of damaged hair include brittle or harsh texture, split ends, breakage, itchy scalp and loss of elasticity. Damaged hair tends to tangle easily and can be difficult to manage and style. Hair becomes damaged in a variety of ways. Hair is typically degraded to varying degrees by the action of atmospheric conditions or by treatments to the hair (e.g., bleaching, curling, straightening, coloring). Once damaged, hair becomes difficult to comb and style and may loose strength and elasticity.

To revitalize and repair the resultant damage to hair various hair care products are marketed for home and professional use. For example, a vast assortment of conditioning compositions have been formulated to impart the feel of softness or smoothness to the hair; to improve the luster, body, manageability, combability of the hair; to impart the hair with increased elasticity and/or an overall appealing appearance. Conditioning of hair is effected by applying a composition to the hair that serves to impart hair with one of the noted properties.

Notwithstanding, there remains a need for improved hair conditioning formulations and methods of making the same, which methods expand the palate of easily incorporated ingredients to include the incorporation of ingredients with desirable hair care properties that exhibiting physical-chemical properties that might otherwise limit their system compatibility. In particular, even where a given component might provide desirable performance, it may remain unavailable for formulators based on the difficult of incorporating that component into a final shelf stable composition. For instance, solid components that are challenging to disperse in water significant barriers for adoption in product formulations due to associated product processing complications.

Accordingly, what is needed is a hair care system concentrate incorporating difficult to process solid components, wherein the hair care system concentrate is stable and easily incorporated into final aqueous hair care compositions.

The present invention provides a hair care system concentrate, comprising: 9 to 15 wt % of a cellulose based cationic polymer; 39 to 60 wt % a polyalkylene glycol; 9 to 15 wt % a film forming nonionic polyethylene glycol polymer; 2.5 to 20 wt % a linear polypropylene glycol; and, 10 to 35 wt % a polyethylene glycol diester of stearic acid.

The present invention provides a hair care system concentrate, comprising: 9 to 15 wt % of a cellulose based cationic polymer, wherein the cellulose based cationic polymer is selected from the group consisting of polyquaternium-10, polyquaterniums-24, polyquaternium-27, polyquaternium-67, polyquaternium-72 and mixtures thereof; 39 to 60 wt % a polyalkylene glycol, wherein the polyalkylene glycol is according to formula I

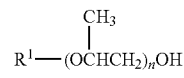

wherein $R^1$ is a $C_{2-20}$ alkyl group; and wherein n has an average value of 10 to 20; 9 to 15 wt % a film forming nonionic polyethylene glycol polymer, wherein the film forming nonionic polyethylene glycol polymer is according to formula II

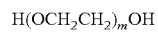

wherein m has an average value of 13,000 to 92,000; 2.5 to 9 wt % a linear polypropylene glycol, wherein the linear polypropylene glycol has an average of two terminal hydroxyl groups per molecule and a weight average molecular weight of 350 to 600 Daltons; and, 10 to 35 wt % a polyethylene glycol diester of stearic acid, wherein the polyethylene glycol diester of stearic acid is according to formula III

wherein x has an average value of 130 to 170.

The present invention provides a hair care system concentrate, comprising: 9 to 15 wt % of a cellulose based cationic polymer, wherein the cellulose based cationic polymer is polyquaternium-67; 39 to 60 wt % a polyalkylene glycol, wherein the polyalkylene glycol is according to the formula I, wherein $R^1$ is a $C_4$ alkyl group and wherein n has an average value of 12 to 16; 9 to 15 wt % a film forming nonionic polyethylene glycol polymer, wherein the film forming nonionic polyethylene glycol polymer is according to the formula II, wherein m has an average value of 42,000 to 47,000; 2.5 to 9 wt % a linear polypropylene glycol, wherein the linear polypropylene glycol has a weight average molecular weight of 400 to 450 Daltons; and, 10 to 35 wt % a polyethylene glycol diester of stearic acid, wherein the polyethylene glycol diester of stearic acid is according to the formula III, wherein x has an average value of 140 to 160.

The present invention provides a hair care system concentrate, comprising: 11 to 13 wt % of the cellulose based cationic polymer, wherein the cellulose based cationic polymer is polyquaternium-67; 51 to 53 wt % of the polyalkylene glycol, wherein the polyalkylene glycol is according to the formula I, wherein $R^1$ is a $C_4$ alkyl group and wherein n has an average value of 14; 11 to 12 wt % of the film forming nonionic polyethylene glycol polymer according to formula II, wherein m has an average value of 42,000 to 47,000; 4 to 6 wt % of the linear polypropylene glycol, wherein the linear polypropylene glycol has an average of two terminal hydroxyl groups per molecule and a weight average molecular weight of 400 to 450 Daltons; and, 18 to 20 wt % of the polyethylene glycol diester of stearic acid, wherein the polyethylene glycol diester of stearic acid is according to the formula III, wherein x has an average value of 140 to 160.

The present invention provides a method of making a hair care system concentrate, comprising: providing a cellulose based cationic polymer; providing a polyalkylene glycol; providing a film forming nonionic polyethylene glycol polymer; providing a linear polypropylene glycol; providing a polyethylene glycol diester of stearic acid; heating the linear polypropylene glycol and the polyethylene glycol diester of stearic acid to ≤65° C.; combining the linear polypropylene glycol and the polyethylene glycol diester of stearic acid to form a combination; then adding the polyalkylene glycol to the combination while allowing the temperature of the combination to cool to ≤45° C.; and, then adding the cellulose based cationic polymer and the film forming nonionic polyethylene glycol polymer to the combination to form the hair care system concentrate.

DETAILED DESCRIPTION

We have now surprising found a unique hair care system concentrate that is both stable and capable of incorporating high concentrations of certain desirable hair care components that happen to be hydrophobic and appropriate concentrations of certain desirable hair care compositions that happen to be hydrophilic and solid at room temperature and capable of easy incorporation into hair care formulations (e.g., hair care conditioners and hair care shampoos).

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modem Size Exclusion Chromatography, W. W. Yau, J. J. Kirkland, D. D. Bly; Wiley-lnterscience, 1979, and in A Guide to Materials Characterization and Chemical Analysis, J. P. Sibilia; VCH, 1988, p.81-84. Molecular weights are reported herein in units of Daltons.

The term "polymer" as used herein and in the appended claims refers to a compound prepared by polymerizing monomers, whether of the same or a different type. The generic term "polymer" includes the terms "homopolymer," "copolymer," and "terpolymer."

The term "hair care" as used herein and in the appended claims relates to concentrates formulated for use in the preparation of compositions for topical application to hair, in particular, to human hair. Examples of such compositions include, but are not limited to, leave-on hair conditioners, rinse off hair conditioners, shampoos, styling gels, hair masks and combing creams.

The term "cosmetically acceptable" as used herein and in the appended claims refers to ingredients typically used in hair care compositions, and is intended to underscore that materials that are toxic when present in the amounts typically found in hair care compositions are not contemplated as part of the present invention.

The term "stable" as used herein and in the appended claims in reference to the hair care system concentrate means that the hair care system concentrate does not display syneresis apparent by unaided visual observation.

The term "storage stable" as used herein and in the appended claims in reference to the hair care system concentrate means that the hair care system concentrate does not display syneresis apparent by unaided visual observation during storage of the hair care system concentrate at 25° C. for a period of at least twelve (12) weeks.

The term "enhanced storage stability" as used herein and in the appended claims in reference to the hair care system concentrate means that the hair care system concentrate does not display syneresis apparent by unaided visual observation during storage of the hair care system concentrate at a temperature of 5 to 45° C. for a period of at least twelve (12) weeks.

Preferably, the hair care system concentrate of the present invention, comprises: 9 to 15 wt % (preferably, 10 to 14; more preferably 11 to 13; most preferably, 12 wt %) of a cellulose based cationic polymer (preferably, wherein the cellulose based cationic polymer is selected from the group consisting of polyquaternium-10, polyquaterniums-24, polyquaternium-27, polyquaternium-67, polyquaternium-72 and mixtures thereof); 39 to 60 wt % (preferably, 45 to 58 wt %; more preferably, 51 to 53 wt %; most preferably, 52 wt %) a polyalkylene glycol (preferably, wherein the polyalkylene glycol is according to formula I

wherein IV is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14)); 9 to 15 wt% (preferably, 10 to 14; more preferably 11 to 13; most preferably, 12 wt %) a film forming nonionic polyethylene glycol polymer (preferably, wherein the film forming nonionic polyethylene glycol polymer is according to formula II

wherein m has an average value of 13,000 to 92,000 (preferably, 35,000 to 80,000; more preferably, 40,000 to 50,000; yet more preferably, 42,000 to 47,000; most preferably, 44,000 to 46,000)); 2.5 to 20 wt % (preferably, 2.5 to 10 wt %; more preferably, 3 to 7.5 wt %; yet more preferably, 4 to 6 wt %; most preferably, 5 wt %) a linear polypropylene glycol (preferably, wherein the linear polypropylene glycol has an average of two terminal hydroxyl groups per molecule and a weight average molecular weight of 350 to 600 Daltons)); and, 10 to 35 wt % (preferably, 16 to 25 wt %; more preferably, 18 to 20 wt %; most preferably, 19 wt %) a polyethylene glycol diester of stearic acid (preferably, wherein the polyethylene glycol diester of stearic acid is according to formula III

wherein x has an average value of 130 to 170 (preferably, 140 to 160; more preferably, 145 to 155; most preferably, 150)).

Preferably, the hair care system concentrate of the present invention is stable. More preferably, the hair care system concentrate of the present invention is storage stable. Most preferably, the hair care system concentrate of the present invention has enhanced storage stability.

Preferably, the cellulose based cationic polymer used in the hair care system concentrate of the present invention is a cosmetically acceptable cellulose based cationic polymer. More preferably, the cellulose based cationic polymer used in the hair care system concentrate of the present invention is a cosmetically acceptable cellulose based cationic polymer, wherein the cellulosed based cationic polymer is selected from the group consisting of polyquaternium-10, polyquaterniums-24, polyquaternium-27, polyquaternium-67, polyquaternium-72 and mixtures thereof. Most preferably, the cellulose based cationic polymer is polyquaternium-67.

Preferably, the hair care system concentrate of the present invention contains 9 to 15 wt % of a cellulose based cationic polymer. More preferably, the hair care system concentrate of the present invention contains 10 to 14 wt % of a cellulose based cationic polymer. Still more preferably, the hair care system concentrate of the present invention contains 11 to 13 wt % of a cellulose based cationic polymer. Most preferably, the hair care system concentrate of the present invention contains 12 wt % of a cellulose based cationic polymer.

Preferably, the polyalkylene glycol used in the hair care system concentrate of the present invention is a cosmetically acceptable polyalkylene glycol. More preferably, the polyalkylene glycol used in the hair care system concentrate of the present invention is a cosmetically acceptable polyalkylene glycol, wherein the polyalkylene glycol is according to formula I

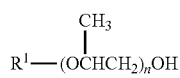

wherein $R^1$ is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14). Most preferably, the polyalkylene glycol is according to the formula I, wherein n has an average value of 12 to 16.

Preferably, the hair care system concentrate of the present invention contains 39 to 60 wt % of a polyalkylene glycol. More preferably, the hair care system concentrate of the present invention contains 45 to 58 wt % of a polyalkylene glycol. Still more preferably, the hair care system concentrate of the present invention contains 51 to 53 wt % of a polyalkylene glycol. Most preferably, the hair care system concentrate of the present invention contains 52 wt % of a polyalkylene glycol.

Preferably, the film forming nonionic polyethylene glycol polymer used in the hair care system concentrate of the present invention is a cosmetically acceptable film forming nonionic polyethylene glycol polymer. Preferably, the film forming nonionic polyethylene glycol polymer used in the hair care system concentrate of the present invention is a cosmetically acceptable film forming nonionic polyethylene glycol polymer, wherein the film forming nonionic polyethylene glycol polymer is according to formula II

wherein m has an average value of 13,000 to 92,000. More preferably, the film forming nonionic polyethylene glycol polymer used in the hair care system concentrate of the present invention is a cosmetically acceptable film forming nonionic polyethylene glycol polymer, wherein the film forming nonionic polyethylene glycol polymer is according to formula II, wherein m has an average value of 35,000 to 80,000. Still more preferably, the film forming nonionic polyethylene glycol polymer used in the hair care system concentrate of the present invention is a cosmetically acceptable film forming nonionic polyethylene glycol polymer, wherein the film forming nonionic polyethylene glycol polymer is according to formula II, wherein m has an average value of 40,000 to 50,000. Yet still more preferably, the film forming nonionic polyethylene glycol polymer used in the hair care system concentrate of the present invention is a cosmetically acceptable film forming nonionic polyethylene glycol polymer, wherein the film forming nonionic polyethylene glycol polymer is according to formula II, wherein m has an average value of 42,000 to 47,000. Most preferably, the film forming nonionic polyethylene glycol polymer used in the hair care system concentrate of the present invention is a cosmetically acceptable film forming nonionic polyethylene glycol polymer, wherein the film forming nonionic polyethylene glycol polymer is according to formula II, wherein m has an average value of 44,000 to 46,000.

Preferably, the hair care system concentrate of the present invention contains 9 to 15 wt % of a film forming nonionic polyethylene glycol polymer. More preferably, the hair care system concentrate of the present invention contains 10 to 14 wt % of a film forming nonionic polyethylene glycol polymer. Still more preferably, the hair care system concentrate of the present invention contains 11 to 13 wt % of a film forming nonionic polyethylene glycol polymer. Most preferably, the hair care system concentrate of the present invention contains 12 wt % of a film forming nonionic polyethylene glycol polymer.

Preferably, the linear polypropylene glycol used in the hair care system concentrate of the present invention is a cosmetically acceptable linear polypropylene glycol. More preferably, the linear polypropylene glycol used in the hair care system concentrate of the present invention is a cosmetically acceptable linear polypropylene glycol, wherein the linear polypropylene glycol has an average of two terminal hydroxyl groups per molecule and a weight average molecular weight of 350 to 600 Daltons. Still more preferably, the linear polypropylene glycol used in the hair care system concentrate of the present invention is a cosmetically acceptable linear polypropylene glycol, wherein the linear polypropylene glycol has an average of two terminal hydroxyl groups per molecule and a weight average molecular weight of 410 to 440 Daltons. Yet still more preferably, the linear polypropylene glycol used in the hair care system concentrate of the present invention is a cosmetically acceptable linear polypropylene glycol, wherein the linear polypropylene glycol has an average of two terminal hydroxyl groups per molecule and a weight average molecular weight of 420 to 430 Daltons. Most preferably, the linear polypropylene glycol used in the hair care system concentrate of the present invention is a cosmetically acceptable linear polypropylene glycol, wherein the linear polypropylene glycol has an average of two terminal hydroxyl groups per molecule and a weight average molecular weight of 425 Daltons.

Preferably, the hair care system concentrate of the present invention contains 2.5 to 20 wt % of a linear polypropylene glycol. More preferably, the hair care system concentrate of the present invention contains 2.5 to 10 wt % of a linear polypropylene glycol. Yet more preferably, the hair care system concentrate of the present invention contains 3 to 7 wt % of a linear polypropylene glycol. Still more preferably, the hair care system concentrate of the present invention contains 4 to 6 wt % of a linear polypropylene glycol. Most preferably, the hair care system concentrate of the present invention contains 5 wt % of a linear polypropylene glycol.

Preferably, the polyethylene glycol diester of stearic acid used in the hair care system concentrate of the present invention is a cosmetically acceptable polyethylene glycol diester of stearic acid. More preferably, the polyethylene glycol diester of stearic acid used in the hair care system concentrate of the present invention is a cosmetically acceptable polyethylene glycol diester of stearic acid, wherein the polyethylene glycol diester of stearic acid is according to formula III

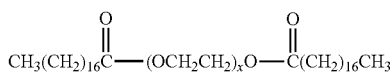
III wherein x has an average value of 130 to 170. Still more preferably, the polyethylene glycol diester of stearic acid used in the hair care system concentrate of the present invention is a cosmetically acceptable polyethylene glycol diester of stearic acid, wherein the polyethylene glycol diester of stearic acid is according to formula III, wherein x has an average value of 140 to 160. Yet still more preferably, the polyethylene glycol diester of stearic acid used in the hair care system concentrate of the present invention is a cosmetically acceptable polyethylene glycol diester of stearic acid, wherein the polyethylene glycol diester of stearic acid is according to formula III, wherein x has an average value of 145 to 155. Most preferably, the polyethylene glycol diester of stearic acid used in the hair care system concentrate of the present invention is a cosmetically acceptable polyethylene glycol diester of stearic acid, wherein the polyethylene glycol diester of stearic acid is according to formula III, wherein x has an average value of 150.

Preferably, the hair care system concentrate of the present invention contains 10 to 35 wt % of a polyethylene glycol diester of stearic acid. More preferably, the hair care system concentrate of the present invention contains 16 to 25 wt % of a polyethylene glycol diester of stearic acid. Still more preferably, the hair care system concentrate of the present invention contains 18 to 20 wt % of a polyethylene glycol diester of stearic acid. Most preferably, the hair care system concentrate of the present invention contains 19 wt % of a polyethylene glycol diester of stearic acid.

Preferably, the method of making a hair care system concentrate of the present invention, comprises: providing a cellulose based cationic polymer (preferably, wherein the cellulose based cationic polymer is a cosmetically acceptable cellulosed based cationic polymer selected from the group consisting of polyquaternium-10, polyquaternium-24, polyquaternium-27, polyquaternium-67, polyquaternium-72 and mixtures thereof); providing a polyalkylene glycol (preferably, wherein the polyalkylene glycol is a cosmetically acceptable polyalkylene glycol according to formula I

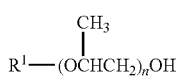
I wherein $R^1$ is a $C_{2-20}$ alkyl group (preferably, a $C_{4-18}$ alkyl group; more preferably, a $C_{4-10}$ alkyl group; most preferably, a $C_4$ alkyl group); and wherein n has an average value of 10 to 20 (preferably, 12 to 16; more preferably, 13 to 15; most preferably, 14)); providing a film forming nonionic polyethylene glycol polymer (preferably, wherein the film forming nonionic polyethylene glycol polymer is a cosmetically acceptable polyalkylene glycol according to formula II

wherein m has an average value of 13,000 to 92,000 (preferably, 35,000 to 80,000; more preferably, 40,000 to 50,000; yet more preferably, 42,000 to 47,000; most preferably, 44,000 to 46,000)); providing a linear polypropylene glycol (preferably, wherein the linear polypropylene glycol is a cosmetically acceptable linear polypropylene glycol having an average of two terminal hydroxyl groups per molecule and a weight average molecular weight of 350 to 600 Daltons); providing a polyethylene glycol diester of stearic acid (preferably, wherein the polyethylene glycol diester of stearic acid is a cosmetically acceptable polyethylene glycol diester of stearic acid according to formula III

III wherein x has an average value of 130 to 170 (preferably, 140 to 160; more preferably, 145 to 155; most preferably, 150)); heating the linear polypropylene glycol and the polyethylene glycol diester of stearic acid to >65° C. (preferably, 65 to 100° C.; more preferably, 65 to 80° C.; most preferably, 70 to 75° C.); combining the linear polypropylene glycol and the polyethylene glycol diester of stearic acid (preferably, with agitation) to form a combination; then adding the polyalkylene glycol to the combination (preferably, with continued agitation) while allowing the temperature of the combination to cool to ≤45° C.; and, then adding the cellulose based cationic polymer and the film forming nonionic polyethylene glycol polymer to the combination (preferably, with continued agitation) to form the hair care system concentrate.

Some embodiments of the present invention will now be described in detail in the following Examples.

Examples 1-2: Preparation Hair Care System Concentrate

In each of Examples 1-2, a hair care system concentrate having the composition noted in TABLE 1 was prepared in a flask outfitted with a heating mantle and a stirring bar. PPG-9 (Polyglycol P425 "P" series polyglycol available from The Dow Chemical Company) was added to the flask and heated to a temperature of 70 to 75° C. Then PEG 150 distearate (Aculyn™ 60 polymer available from The Dow Chemical Company) was added to the flask with stirring for about 10 minutes while maintaining the temperature set point at 70 to 75° C. to provide a homogenous mixture. The heating mantle was then removed from the flask and PPG-14 butyl ether (Ucon™ fluid AP available from The Dow Chemical Company) was introduced to the flask contents slowly over a period of about 10 minutes with continued stirring. The flask contents were then allowed to continue cooling to 45° C. A premixture of polyquaternium-67 (Softcat™ SX Polymer SX-1300X available from The Dow Chemical Company) and PEG-45M (Polyox™ WSR N60K available from The Dow Chemical Company) were then slowly added to the flask contents with continued stirring. Then continue stirring the contents of the flask for 40 to 50 minutes to provide the product hair care system concentrate.

TABLE 1

| Component | | Final system concentration (wt %) | |
|---|---|---|---|
| INCI Name | Commercial Name[a] | Ex. 1 | Ex. 2 |
| PPG-9 | Polyglycol P425 | 5.0 | 18.0 |
| PPG-14 butyl ether | Ucon™ Fluid AP | 52.0 | 42.0 |
| Polyquaternium-67 | Softcat™ SX Polymer SX-1300X | 12.0 | 15.0 |
| PEG-45M | Polyox™ WSR N60K | 12.0 | 15.0 |
| PEG150 Distearate | Aculyn™ 60 polymer | 19.0 | 10.0 |

[a]Available from The Dow Chemical Company

Stability Evaluations

The stability of a hair care system concentrates prepared according to Examples 1 and 2 were evaluated over a three month period. Each of the hair care system concentrates was divided into three samples. One sample was maintained at 5° C. over the three month period. A second sample was maintained at 25° C. over the three month period. A third sample was maintained at 45° C. over the three month period. The evaluation included a visual assessment and an evaluation of the rheological behavior of each of the three samples of the hair care system concentrate. Visual inspection of the samples over the three month period showed no syneresis in any of the samples. The visual inspection did show some yellowing of the hair care system concentrate over the three month period in the sample maintained at 45° C. The rheological behavior of the sample of the hair care system concentrate maintained at 25° C. remained unchanged over the thirty day period. A slight drop in the viscosity was observed for the samples of the hair care system concentrate maintained at 5° C. and at 4° C.

Comparative Example C1: Order of Addition

Comparative combinations having the same composition noted in TABLE 1 were prepared using the same flask outfitted with a heating mantle and a stirring bar as used in Example 1. In the comparative combinations of Comparative Example C1, the order of addition of the various components were modified. From these comparative combinations, it was determined critical that the PEG150 Distearate be added to the flask before the PPG-14 butyl ether, the polyquaterniums-67 and the PEG-45M to avoid liquid separation or syneresis in the product obtained.

Comparative Example C2: Temperature when Added

Comparative combinations having the same composition noted in TABLE 1 were prepared using the same flask outfitted with a heating mantle and a stirring bar as used in Example 1. In the comparative combinations of Comparative Example C2, the components were added to the flask in the same order as in Example 1. In contrast to Example 1, however, the temperature of the flask contents were >45° C. when the polyquaterniums-67 and the PEG-45M were added to the flask in each of the comparative combinations of Comparative Example C2, resulting in a thick paste.

Comparative Example C3: Film Forming Nonionic Polyethylene Glycol Polymer

Comparative combinations having the same composition noted in TABLE 1 with the exception that the PEG-45M was substituted with PEG-90M (Polyox™ WSR N301 available from The Dow Chemical Company) was prepared using the same flask outfitted with a heating mantle and a stirring bar as used in Example 1. The resulting composition was extremely elastic and was not amenable to pumping.

Comparative Example C4: Polyethylene Glycol Diester of Stearic Acid Concentration A plurality of hair care system concentrates were prepared having the same component content as present in Example 1 with the exception that the amount of PEG150 distearate added was varied to provide a dosage concentration thereof in the final system concentrate ranging from 3 to 20 wt %. The hair care system concentrates having a PEG150 distearate concentration of 10 to 19 wt % were observed not to exhibit syneresis.

Example 3: Hair Care Composition

A hair care system concentrate prepared according to Example 1 was added to an aqueous base conditioner formulation to provide a product aqueous hair care conditioner composition as described in TABLE 2.

TABLE 2

| Ingredient | wt % |
|---|---|
| Stearamidopropyl dimethylamine | 1.50 |
| Cethearyl alcohol | 5.00 |
| Lactic acid, 85% | 0.52 |
| BHT | 0.05 |
| Dissodium EDTA | 0.10 |
| Behentrimonium chloride | 0.30 |
| Preservative | 0.50 |
| Hair care system concentrate | 1.50 |

We claim:
1. A hair care system concentrate, comprising:
9 to 15 wt % of a cellulose based cationic polymer; wherein the cellulose based cationic polymer is selected from the group consisting of polyquaternium-10, polyquaterniums-24, polyquaternium-27, polyquaternium-67, polyquaternium-72 and mixtures thereof;
39 to 60 wt % a polyalkylene glycol; wherein the polyalkylene glycol is according to formula I

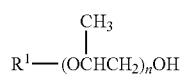

I $$R^1\!-\!(OCHCH_2)_n OH \quad \text{with CH}_3 \text{ branch}$$

wherein $R^1$ is a $C_{2-20}$ alkyl group; and wherein n has an average value of 10 to 20;
9 to 15 wt % a film forming nonionic polyethylene glycol polymer; wherein the film forming nonionic polyethylene glycol polymer is according to formula II

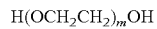

$$H(OCH_2CH_2)_m OH \quad \text{II}$$

wherein m has an average value of 13,000 to 92,000;
2.5 to 20 wt % a linear polypropylene glycol; wherein the linear polypropylene glycol has an average of two terminal hydroxyl groups per molecule and a weight average molecular weight of 350 to 600 Daltons; and, 10 to 35 wt % a polyethylene glycol diester of stearic acid; wherein the polyethylene glycol diester of stearic acid is according to formula III

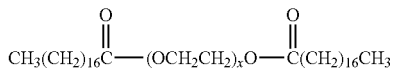

III wherein x has an average value of 130 to 170.

2. The hair care system concentrate of claim 1,
wherein the cellulose based cationic polymer is polyquaternium-67;
wherein n has an average value of 12 to 16;
wherein m has an average value of 42,000 to 47,000;
wherein the linear polypropylene glycol has a weight average molecular weight of 350 to 600 Daltons; and,
wherein x has an average value of 140 to 160.

3. The hair care system concentrate of claim 2, wherein $R^1$ is a $C_4$ alkyl group.

4. The hair care system concentrate of claim 2, wherein m has an average value of 44,000 to 46,000.

5. The hair care system concentrate of claim 2, wherein the linear polypropylene glycol has a weight average molecular weight of 420 to 430 Daltons.

6. The hair care system concentrate of claim 2, wherein x has an average value of 145 to 155.

7. The hair care system concentrate of claim 2, wherein the cellulose based cationic polymer is polyquaternium-67; wherein $R^1$ is a $C_4$ alkyl group; and wherein n has an average value of 12 to 16;
wherein m has an average value of 42,000 to 47,000;
wherein the linear polypropylene glycol has a weight average molecular weight of 410 to 440 Daltons; and
wherein x has an average value of 140 to 160.

8. The hair care system concentrate of claim 1, wherein the hair care system concentrate comprises:
11 to 13 wt % of the cellulose based cationic polymer, wherein the cellulose based cationic polymer is polyquaternium-67;
51 to 53 wt % of the polyalkylene glycol, wherein $R^1$ is a $C_4$ alkyl group; and wherein n has an average value of 14;
11 to 12 wt % of the film forming nonionic polyethylene glycol polymer according to formula II,
wherein m has an average value of 42,000 to 47,000;
4 to 6 wt % of the linear polypropylene glycol, wherein the linear polypropylene glycol has a weight average molecular weight of 400 to 450 Daltons; and,
18 to 20 wt % of the polyethylene glycol diester of stearic acid, wherein x has an average value of 140 to 160.

9. A method of making a hair care system concentrate, comprising:
providing a cellulose based cationic polymer;
providing a polyalkylene glycol;
providing a film forming nonionic polyethylene glycol polymer;
providing a linear polypropylene glycol;
providing a polyethylene glycol diester of stearic acid;
heating the linear polypropylene glycol and the polyethylene glycol diester of stearic acid to 65 to 80° C.;
combining the linear polypropylene glycol and the polyethylene glycol diester of stearic acid to form a combination;
then adding the polyalkylene glycol to the combination while allowing the temperature of the combination to cool to ≤45° C.; and,
then adding the cellulose based cationic polymer and the film forming nonionic polyethylene glycol polymer to the combination to form the hair care system concentrate.

* * * * *